US008835178B2

(12) United States Patent
Farquar et al.

(10) Patent No.: US 8,835,178 B2
(45) Date of Patent: *Sep. 16, 2014

(54) BIO-THREAT MICROPARTICLE SIMULANTS

(75) Inventors: George Roy Farquar, Livermore, CA (US); Roald Leif, San Ramon, CA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/608,962

(22) Filed: Sep. 10, 2012

(65) Prior Publication Data

US 2013/0052751 A1     Feb. 28, 2013

Related U.S. Application Data

(63) Continuation of application No. 12/909,128, filed on Oct. 21, 2010, now Pat. No. 8,293,535.

(60) Provisional application No. 61/257,242, filed on Nov. 2, 2009.

(51) Int. Cl.
| G01N 31/00 | (2006.01) |
| C12Q 1/68 | (2006.01) |
| A61K 9/127 | (2006.01) |
| G01N 1/00 | (2006.01) |
| G01N 21/64 | (2006.01) |
| C07K 14/00 | (2006.01) |

(52) U.S. Cl.
CPC ............ G01N 21/6428 (2013.01); A61K 9/127 (2013.01); G01N 1/00 (2013.01); C07K 14/00 (2013.01)
USPC ........ 436/8; 436/9; 436/20; 436/94; 436/174; 436/181; 435/6.1; 252/408.01

(58) Field of Classification Search
USPC ............... 436/8, 9, 15, 20, 94, 174, 181, 183; 435/6.1; 252/408.1
See application file for complete search history.

(56) References Cited

U.S. PATENT DOCUMENTS

| 6,197,229 B1 * | 3/2001 | Ando et al. .................... 264/4.1 |
| 7,030,097 B1 * | 4/2006 | Saltzman et al. ............ 514/44 R |
| 7,781,224 B2 | 8/2010 | Martin et al. |
| 8,293,535 B2 * | 10/2012 | Farquar et al. .................... 436/8 |
| 2002/0172717 A1 * | 11/2002 | Leong et al. .................. 424/499 |
| 2009/0221087 A1 * | 9/2009 | Martin et al. ................. 436/172 |
| 2014/0057276 A1 | 2/2014 | Farquar et al. |

OTHER PUBLICATIONS

Dana A. Shea, "The Bio Watch Program: Detection of Bioterrorism". Congressional Research Service Report No. RL 32152, Nov. 19, 2003.

* cited by examiner

*Primary Examiner* — Maureen Wallenhorst
(74) *Attorney, Agent, or Firm* — Dominic M. Kotab

(57) ABSTRACT

A bio-threat simulant that includes a carrier and DNA encapsulated in the carrier. Also a method of making a simulant including the steps of providing a carrier and encapsulating DNA in the carrier to produce the bio-threat simulant.

41 Claims, 2 Drawing Sheets

BIO-THREAT MICROPARTICLE SIMULANTS

CROSS-REFERENCE TO RELATED APPLICATIONS

The present application is a continuation of U.S. application Ser. No. 12/909,128, filed on Oct. 21, 2010, entitled "Bio-Threat Microparticle Simulants", now U.S. Pat. No. 8,293,535, issued on Oct. 23, 2012, which is a non-provisional application claiming priority to U.S. Provisional Patent Application No. 61/257,242 filed Nov. 2, 2009, now expired, the entire contents and disclosures of which are hereby incorporated by reference herein.

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to testing and more particularly to safe and effective stimulants for testing.

2. State of Technology

U.S. Pat. No. 7,781,224 issued Aug 24, 201 to Sue I. Martin et al titled "Safe Biodegradable Fluorescent Particles," assigned to Lawrence Livermore, National Security, LLC., provides the following state of technology information:

> The present invention provides a "safe" fluorescent particle for a variety of applications. The particle comprises a non-biological, biodegradable carrier and natural fluorophores encapsulated in the non-biological, biodegradable carrier. In some embodiments the particle is used as a simulant for mimicking the fluorescence properties of microorganisms. However, the particle need not mimic the fluorescent characteristics of a microorganism, rather it can be incorporated into one or more natural fluorophores as a means for fluorescence detection. Single or combinations of fluorophores are encapsulated to produce a desired fluorescent effect such as particles that fluoresce at 370 nm maxima. The particles can therefore be tuned to the excitation wavelength of a fluorescence detector.
>
> One application for these particles is their use in aerosol studies, such as large scale air dispersal to track particulate migration over vast areas, or for urban particle dispersion studies. Currently, researchers performing these studies rely on air dispersion models and gas tracer tests to determine the movement and flow of aerosols in urban environments such as in cities—around and through occupied buildings—because "safe" particles are not available. These particles would provide those safety benefits. Furthermore, these particles could be designed with the appropriate density and perhaps shape of a microorganism to mimic the aerodynamic movement of a microorganism.
>
> An example of aerosol study is described in the article, "An examination of the urban dispersion curves derived from the St. Louis dispersion study" by Akula Venkatram in *Atmospheric Environment* 39 (2005) 3813-3822, which describes a study, "The St. Louis study was conducted over the period 1963-1965. The study consisted of a series of 26 daytime and 16 evening experiments in which fluorescent zinc cadmium sulfide particles were released near ground level at two different locations under a variety of meteorological conditions. During the first year of the experiments, the release was at ground level in a relatively open area in a park located west of the downtown area. In the second year, the tracer was released from the top of a three-story building surrounded by trees and similar buildings. The main downtown area, consisting of buildings with an average height of 40 m, was about 5 km away from both release locations." The disclosure of the article, "An examination of the urban dispersion curves derived from the St. Louis dispersion study" by Akula Venkatram in *Atmospheric Environment* 39 (2005) 3813-3822 is incorporated herein by this reference.
>
> Another example of aerosol study is described in the article, "Use of Salt Lake City URBAN 2000 Field Data to Evaluate the Urban Hazard Prediction Assessment Capability (HPAC) Dispersion Model" by Joseph C. Chang in JOURNAL OF APPLIED METEOROLOGY pages 485-501 (2005) which provides background about the study, "The potential impacts of the atmospheric release of chemical, biological, radiological, and nuclear (CBRN) or other hazardous materials are of increasing concern. Hazardous releases can occur due to accidents, such as the release of toxic industrial chemicals in Bhopal, India, in 1984 (e.g., Sharan et al. 1996) and the Chernobyl nuclear power plant disaster in the Ukraine in 1986 (e.g., Puhakka et al. 1990). They can also occur as an unintentional result of military actions, such as the U.S. destruction of rockets with chemical warheads at Khamisiyah, Iraq, after the 1991 Gulf War (Winkenwerder 2002). More recently, terrorist incidents in urban settings, such as the events on 11 Sep. 2001 in New York City, N.Y., and Washington, D.C., and military conflicts dramatically raise concerns for the possibility of mass casualties." The disclosure of the article, "Use of Salt Lake City URBAN 2000 Field Data to Evaluate the Urban Hazard Prediction Assessment Capability (HPAC) Dispersion Model" by Joseph C. Chang in *JOURNAL OF APPLIED METEOROLOGY* pages 485-501 (2005) is incorporated herein by this reference.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

Conducting atmospheric releases in order to challenge detector sensor networks poses unique challenges. With the increasing use of biosensors for the detection of threat agents there is a growing need for a universal biosimulant. The universal simulant needs to have several properties to allow for real world evaluation of biodetector and collection networks. First, the material must be able to be collected and trigger the detector. Second, the simulant must be safe to release in an environment where workers and the public will be exposed to the material. Third, the material must be able to have controllable aerosol properties, such as charge and physical or aerodynamic size. The invention details a low cost, safe, individually designed particle for the use in testing biosensor networks.

The present invention provides a stimulant including a carrier and DNA encapsulated in the carrier. The present invention has all of the desired properties for a universal simulant. Not only will the universal simulant be able to test and evaluate single detectors it will be optimal for the validation of atmospheric release models with multiple sensors. Currently a release study with a single simulant requires a costly experiment for a single release location. If multiple release locations are desired multiple studies must be conducted to allow each release location and transport pathway to be uniquely identified. By using Applicants' new DNA containing biosimulant multiple releases can occur simultaneously. This is accomplished by modifying the unique DNA sequence for the release material. Using unique DNA allows for a near limitless variety of unique particle identifiers.

The microsphere simulant can be used as challenge-test standards for determining sensitivity of detection technologies. The microsphere simulant can be used for large-scale air current deployments or tests for determining the movement and distribution of particles in urban environments. The microsphere simulant can be labeled to distinguish between "test" microspheres and background microorganisms/organic particles. The microsphere simulant can be used as a calibration standard for bio-detectors. The microsphere simulant can be used to train personnel to operate bio- detectors. Surface properties, such as hydrophobicity and surface charge, can be tuned/altered for various applications. The microsphere simulant provides a universal simulant that can be used for field aerosol studies, mock biowarfare training, training for rapid assessment of bioweapons labs, calibrating detection equipment, and other uses.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1:
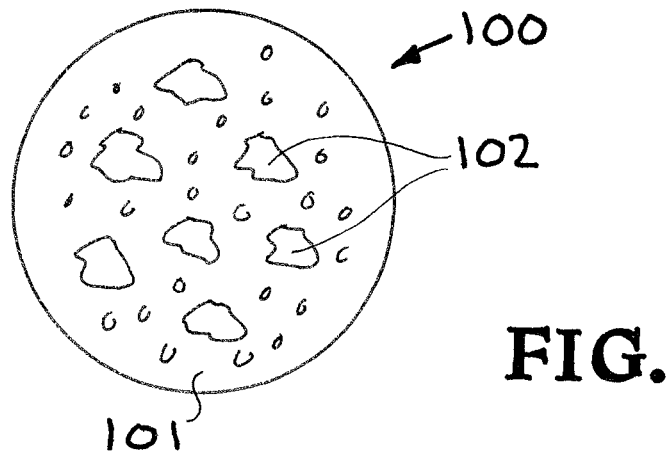
FIG. 1 illustrates a microsphere containing DNA strand and Glucono-delta-lactone (GDL)

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The January/February 2002 issue of Science & Technology Review, in an article titled "Rapid Field Detection of Biological Agents," describes two systems to rapidly detect and identify biological agents, including pathogens such as anthrax and plague. The systems are the Handheld Advanced Nucleic Acid Analyzer (HANAA) and the Autonomous Pathogen Detection System (APDS). About the size of a brick, the HANAA biodetection system can be held in one hand and weighs less than a kilogram. The system was designed for emergency response groups, such as firefighters and police, who are often first on the scene at sites where bioterrorism may have occurred. Each handheld system can test four samples at once—either the same test on four different samples or four different tests on the same sample. HANAA can provide results in less than 30 minutes, compared with the hours to days that regular laboratory tests typically take. To detect the DNA in a sample, a synthesized DNA probe tagged with a fluorescent dye is introduced into the sample before it is inserted into the heater chamber. Each probe is designed to attach to a specific organism, such as anthrax or plague. Thus, the operator must have an idea of what substances might be involved. "The system doesn't test for all unknowns," says Langlois. "A responder has to decide what kinds of pathogens to test for ahead of time and set up the system accordingly." If that organism is present in the sample, the probe attaches to its DNA, which is then amplified during the PCR process, releasing the fluorescent tag. HANAA measures the sample's fluorescence and the presence (or absence) of the targeted organism. Whereas HANAA can be hand-carried to sites at which an attack is suspected to have happened, the APDS is stationed in one place for continuous monitoring and is designed to work much like a smoke detector, but for pathogens. When fully developed, the APDS could be placed in a large area such as an airport, a stadium, or a conference hall. The system will sample the air around the clock and sound an alarm if pathogens are detected. The disclosure of the article titled "Rapid Field Detection of Biological Agents," in the January/February 2002 issue of Science & Technology Review is incorporated herein by this reference.

The October 2004 issue of Science & Technology Review, in an article titled "Detecting Bioaerosols When Time is of the Essence," states that Livermore researchers received seed funding from the Laboratory Directed Research and Development Program to develop an instrument that counters bioterrorism by providing a rapid early warning system for pathogens, such as anthrax. That instrument, the Autonomous Pathogen Detection System (APDS), is now ready for deployment to better protect the public from a bioaerosol attack, and the development team has been honored with a 2004 R&D 100 Award. In September 2003, APDS passed a series of pathogen exposure tests at a high-containment laboratory at the Dugway Proving Ground in Utah. In these trials, the system clearly demonstrated that it could detect real pathogens and confirm the identifications with a fully automated second assay method. APDS units were also deployed at the Albuquerque Airport in New Mexico and at a Washington, D.C., Metro station, where they provided continuous monitoring for up to seven days, unattended. The system can be adapted for situations where environmental or clinical pathogens require monitoring. For example, APDS could test for mold or fungal spores in buildings or for the airborne spread of contagious materials in hospitals. It also could identify disease outbreaks in livestock transport centers or feedlots. The disclosure of the article titled "Detecting Bioaerosols When Time is of the Essence," in the October 2004 issue of Science & Technology Review is incorporated herein by this reference.

The evaluation of different biofluorescence detectors as tools to detect biological attack is currently difficult due to the lack of a single, common standard with which to compare the different instruments. Biological organism stimulants present substantial drawbacks in that they are difficult to transport and aerosolize without damaging them, exposure to them presents a health risk, and they have a tendency to agglomerate, which makes their aerosolization difficult to perform reliably. Furthermore, they have a short shelf life, they are not conveniently disposable, their use requires extensive training, any equipment exposed to them requires bleach or other bactericides/sporicides for cleaning, they are difficult to manufacture, and many aspects of their growth and handling affect their final state. Therefore, biological organisms are not optimal evaluation, calibration, and training standards for biofluorescence instruments. They are, however, fluorescent in the precise manner of a microorganism (obviously), which is ultimately necessary for a test agent or surrogate.

Conducting atmospheric releases in order to challenge detector sensor networks poses unique challenges. With the increasing use of biosensors for the detection of threat agents there is a growing need for a universal biosimulant. The universal simulant needs to possess several properties to allow for real world evaluation of biodetector and collection networks. First, the material must be able to be collected and trigger the detector. Second, the simulant must be safe to release in an environment where workers and the public will be exposed to the material. Third, the material must be able to have controllable aerosol properties, such as charge and physical or aerodynamic size.

The present invention incorporates all of the desired properties. Not only will the universal simulant be able to test and evaluate single detectors it will be optimal for the validation of atmospheric release models with multiple sensors. Currently a model study with a single simulant requires a costly study for a single release location. If multiple locations are desired multiple studies must be conducted. By using Applicants' new DNA containing food safe material multiple releases can occur simultaneously. This is accomplished by modifying the unique DNA sequence for the release material. Using unique DNA allows for a near limitless variety of unique particle codes.

Microsphere Production:

Microspheres are produced to simulate bio-threat agents. The desired size range is in the 1-5 micron diameter. Several methods can be used to produce microsphere particles from liquid solution. The methods discussed focus on aerosolizing the solution and drying the resulting aerosol with a desiccant dryer. The test results discussed focus on the use of an ink jet printer to produce the initial droplets of biosimulant material. This method is used to produce a liquid droplet with reproducible size distributions. Other methods to aerosolize the material are also possible to generate the particles. Other aerosol production methods include salter and collison nebulizers for solution aersolization. The resulting liquid droplets are dried with a desiccant dryer and collected in a chamber or particle impactor. Large quantities of particles may be dried by other methods such as a spray dryers or low humidity counter flow apparatus.

The production of the microspheres with FDA approved food product allows for the ability of ingestion of the material when it is aerosolized. Water soluble food material such as GDL poses minimal risk for inhalation and ease of sample handling in the production process. By using water based material no organic solvents are needed greatly reducing any potential health and safety issues.

EXAMPLES OF THE PRESENT INVENTION

As illustrated in FIG. 1, DNA is combined with a non-toxic food product to produce microspheres simulants. The microsphere simulant is designated generally by the reference numeral 100. The microsphere simulant provides a stimulant that includes a carrier 101 and DNA 102 encapsulated in the carrier 101.

Microspheres 100 are produced by combining DNA 102 a carrier 101 material. The microspheres are produced by dissolving the carrier material and DNA in an aqueous solution and aerosolizing the resulting solution. The material is aerosolized to break the solution into small droplets. The size of the initial droplet and initial concentration of the solution dictates the final particle size. Larger droplets and higher concentration solutions will produce larger particle sizes. The aerosols are dried with a drying apparatus and the microspheres are collected in a collection chamber.

The material is produced by dissolving 10% Glucono-delta-lactone (GDL) and trigger DNA 102 in an aqueous solution. The trigger DNA 102 consists of ~100 DNA bases of thermotoga maritime. With 100 DNA bases and 4 possible substitutions for each base the maximum theoretical total number of unique combinations is $4\hat{}100$ (1.6 e 60). The resulting solution is divided up into droplets with an inkjet print-head or other aerosol production method and the water is removed to produce the simulant. The resulting particle is a safe, size selectable biosimulant containing DNA. By changing the concentration of the GDL or droplet size the size of the dried biosimulant can be selected.

Example 1

Production of Microspheres with a FDA Food Additive and DNA

Glucono-delta-lactone (GDL), a FDA approved kosher certified food additive, was used as the carrier material for the microsphere production. Aqueous solutions of 15% GDL were combined with known amounts of DNA. The aqueous solution was aerosolized with an inkjet printer and the resulting particles were dried with a desiccant dryer. The dried particles were collected on a particle impactor. The results from all production tests at this solution concentration show a size distribution centered at ~1.75 microns. The particles produced contained DNA in the target size range and had a spherical morphology. The size was measured with an aerosol particle sizer and the spherical morphology was confirmed with SEM images.

The mean microsphere size increases linearly with concentration of GDL. This is important, as it shows that the GDL microsphere size may be tailored to the application of interest. As we are interested in producing microspheres between 1 and 5 µm in diameter, we chose 15% GDL as the ideal starting solution to produce microspheres with the desired properties. It is also possible to alter the microsphere size by altering the initial aqueous droplet size. The resulting particle is a safe, size selectable biosimulant containing DNA.

The microsphere simulant 100 can be used as challenge-test standards for determining sensitivity of detection technologies. The microsphere simulant 100 can be used for large-scale air current deployments or tests for determining the movement and distribution of particles in urban environments. The microsphere simulant 100 can be labeled to distinguish between "test" microspheres and background microorganisms/organic particles. The microsphere simulant 100 can be used as a calibration standard for bio-detectors. The microsphere simulant 100 can be used to train personnel to operate bio-detectors. Surface properties, such as hydrophobicity and surface charge, can be tuned/altered for various applications. The microsphere simulant 100 provides a universal simulant that can be used for field aerosol studies, mock biowarfare training, training for rapid assessment of bioweapons labs, calibrating detection equipment, and other uses.

Figure 2:
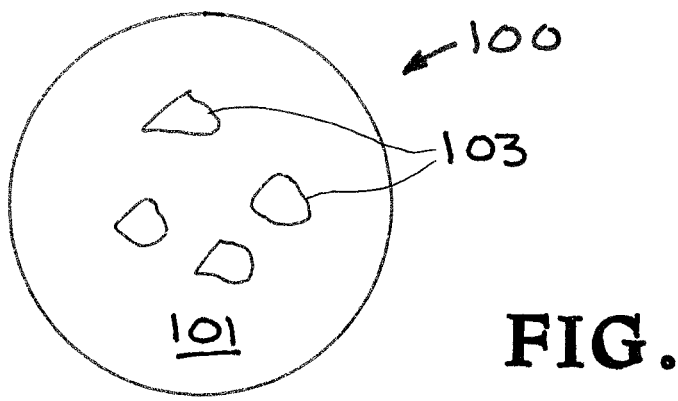
FIG. 2 illustrates a microsphere containing antibody trigger and GDL

As illustrated in FIG. 2, DNA and antibody trigger 103 is combined with carrier material to produce microspheres simulants. The microsphere stimulant is also generally designated by the reference numeral 100 in FIG. 2. The incorporation of the antibody trigger 103 allows the biosimulant 100 to trigger immuno assay detectors. The antibody trigger 103 is added to an aqueous solution of food safe material (currently GDL) or other carrier 101. The resulting solution is aerosolized and dried to form antibody trigger microspheres. It is critical to select the antibody trigger and antibody to take into account any health risks when the particle is released. Many natural antibody triggers such as proteins can cause allergic reactions and this must be taken into account when the trigger material is selected. Antibodies can be produced for a large range of target material ranging from explosives to bovine serum albumin. This diversity of antibodies allows for a large range of potential antibody trigger chemicals. The concentration of antibody trigger and carrier can be easily modified to change both the size of the final particle tuned to select the desired properties for a given experiment.

The microsphere simulant 100 illustrated in FIG. 2 can be used for large-scale air current deployments or tests for determining the movement and distribution of particles in urban environments. The microsphere simulant 100 can be labeled to distinguish between "test" microspheres and background microorganisms/organic particles. The microsphere simulant 100 can be used as a calibration standard for bio-detectors. The microsphere simulant 100 can be used to train personnel to operate bio- detectors. Surface properties, such as hydrophobicity and surface charge, can be tuned/altered for various applications. The microsphere simulant 100 provides a universal simulant that can be used for field aerosol studies, mock biowarfare training, training for rapid assessment of bioweapons labs, calibrating detection equipment, and other uses.

Figure 3:
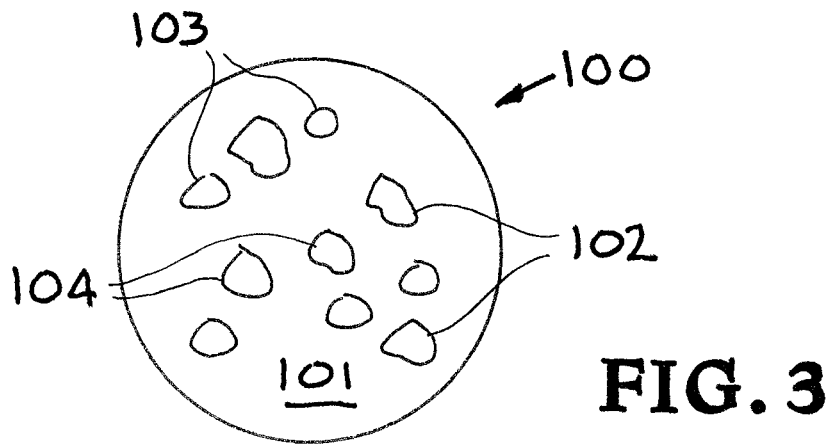
FIG. 3 illustrates a microsphere containing DNA, antibody trigger, fluorophore and GDL

As illustrated in FIG. 3, DNA 102 and antibody triggers 103 and fluorescent molecules 104 are combined with a carrier 101 to produce microspheres stimulants 100. Antibody trigger fluorescent molecules and DNA are added to an aqueous solution of food safe material (currently GDL) or other carrier. By adding multiple fluorescent molecules a unique and tunable fluorescence signal can be achieved. The microsphere simulant 100 illustrated in FIG. 3 can be used for large-scale air current deployments or tests for determining the movement and distribution of particles in urban environments. The microsphere simulant 100 can be labeled to distinguish between "test" microspheres and background microorganisms/organic particles. The microsphere simulant 100 can be used as a calibration standard for bio-detectors. The microsphere simulant 100 can be used to train personnel to operate bio-detectors. Surface properties, such as hydrophobicity and surface charge, can be tuned/altered for various applications. The microsphere simulant 100 provides a universal simulant that can be used for field aerosol studies, mock biowarfare training, training for rapid assessment of bioweapons labs, calibrating detection equipment, and other uses.

Figure 4:
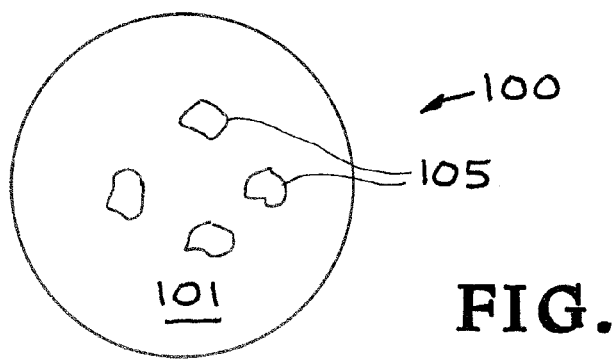
FIG. 4 illustrates a microsphere containing material to control particle transit properties

As illustrated in FIG. 4, materials to alter the particle transport properties 105 are combined with a carrier to produce microspheres 100. Additives are added to a solution of carrier material and the resulting solution is used to produce microspheres. Properties such as charge and density greatly alter aerosol transport properties. By adding material to alter these properties a highly tunable particle can be produced to simulate a natural particle or a threat agent. Being able to reproduce the transport properties of aerosols will allow for more detailed studies of atmospheric release of pollutants and threat materials.

Figure 5:
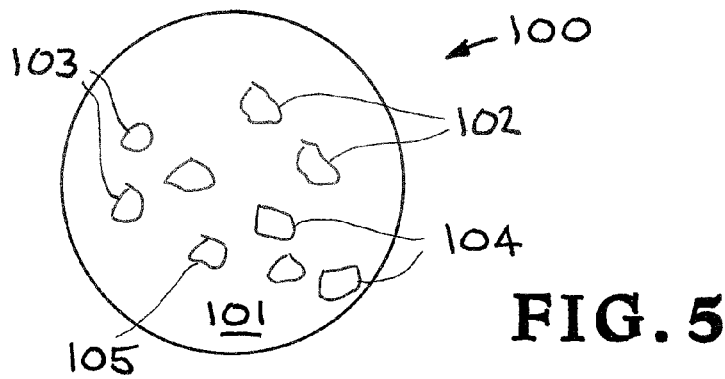
FIG. 5 illustrates a microsphere containing multiple additives combined in a single microsphere
Figure 6:
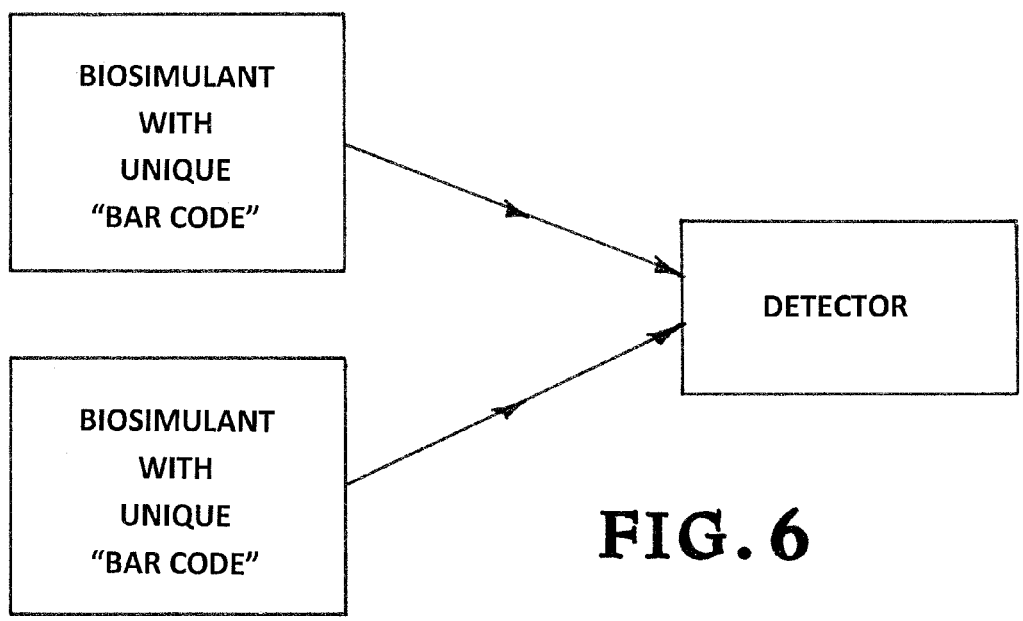
FIG. 6 illustrates how multiple microspheres, each containing unique DNA, enables for simultaneous releases during a single event.

As illustrated in FIG. 5, microspheres with DNA 102, antibody triggers 103, fluorophore 104, and materials 105 to control particle transit properties are combined with a carrier to produce fluorescent microspheres 100. Antibody trigger, fluorescent molecules, additives to control transport properties and DNA are added to an aqueous solution of food safe material (currently GDL) or other carrier. The resulting solution is converted into microspheres.

Multiple varieties of DNA containing microspheres FIG. 1 are produced and simultaneously released to test bio detector networks. Current testing is limited to a small number of testing agents. By using the unique properties and DNA signature for test particles, multiple simultaneous test release can be achieved. This allows for great cost savings and rapid incorporation of real word data into modeling simulations.

Example 2

Glucono-delta-lactone (GDL) a FDA approved kosher certified food additive was used as the carrier material for the microsphere production. Aqueous solutions of 15% GDL were combined with known amounts of DNA. Two sequences of DNA from thermotoga maritime were incorporated into two sets of microsphere particles. The aqueous solution was aerosolized with an inkjet printer. The resulting aerosol was collected and analyzed with PCR. The experiments showed that the resulting aerosol droplets can be identified with PCR.

The trigger DNA consists of ~100 DNA bases of thermotoga maritime. With ~100 DNA bases and 4 possible substitutions for each base the maximum theoretical total number of unique combinations is $4^{100}$ (1.6 e 60).

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A product, comprising:
   a carrier and
   DNA encapsulated in said carrier,
   wherein said carrier comprises one or more materials selected from a group consisting of: a non-toxic food product, and a food additive.

2. The product of claim 1 wherein said carrier includes an FDA approved food additive.

3. The product of claim 1 wherein said carrier includes a kosher certified food additive.

4. The product of claim 1 including a protein encapsulated in said carrier.

5. The product of claim 1 wherein two or more unique DNA are encapsulated in said carrier.

6. The product of claim 1 wherein the food additive comprise Glucono-delta lactone.

7. The product of claim 1 including antibody triggers encapsulated in said carrier.

8. The product of claim 1 including fluorescent molecules combined with and encapsulated in said carrier.

9. The product of claim 1 including antibody triggers and fluorescent molecules combined with and encapsulated in said carrier.

10. The product of claim 1 wherein said carrier has particle transport properties and includes materials combined with and encapsulated in said carrier to alter the particle transport properties of said carrier.

11. The product of claim 1 wherein said carrier has particle transport properties and including materials combined with and encapsulated in said carrier to alter the particle transport properties of said carrier wherein said materials to alter the particle transport properties are materials to alter charge.

12. The product of claim 1 wherein said carrier has particle transport properties and including materials combined with and encapsulated in said carrier to alter the particle transport properties of said carrier wherein said materials to alter the particle transport properties are materials to alter density.

13. The product of claim 1 wherein said carrier has materials to control particle transit properties and wherein said materials to control particle transit properties are combined with and encapsulated in said carrier to control particle transit properties of said carrier.

14. The product of claim 1 including unique DNA, wherein the unique DNA has 100 bases.

15. A product, comprising:
DNA, and
carrier means,
wherein said carrier means is a carrier means made of at least one of: a non-toxic food. product, and a food additive, and
wherein said DNA is encapsulated in said carrier means, 16. The product of claim 15 wherein said carrier means is a carrier means made of FDA approved food additives.

17. The product of claim 15 wherein said carrier means is a carrier means made of kosher certified food additives.

18. The product of claim 15 including a protein encapsulated in said carrier means.

19. The product of claim 15 wherein two or more unique DNA are encapsulated in said carrier means.

20. The product of claim 15 including antibody triggers combined with and encapsulated in said carrier means.

21. The product of claim 15 including fluorescent molecules combined with and encapsulated in said carrier means.

22. The product of claim 15 including antibody triggers and fluorescent molecules combined with and encapsulated in said carrier means.

23. The product of claim 15 wherein said carrier means has particle transport properties and includes materials combined with and encapsulated in said carrier means to alter said particle transport properties of said carrier means.

24. The product of claim 15 wherein said carrier means has particle transport properties and includes materials combined with and encapsulated in said carrier means to alter said particle transport properties of said carrier means wherein said materials to alter said particle transport properties are materials to alter charge.

25. The product of claim 15 wherein said carrier means has particle transport properties and including materials combined with and encapsulated in said carrier means to alter the particle transport properties of said carrier means wherein said materials combined with and encapsulated in said carrier means to alter said particle transport properties are materials to alter density.

26. The product of claim 15 wherein said carrier means has materials to control particle transit properties and wherein said materials to control particle transit properties are combined with and encapsulated in said carrier means to control particle transit properties of said carrier means.

27. The product of claim 15 including unique DNA, wherein the unique DNA has 100 bases.

28. A method, comprising:
providing a carrier, wherein said carrier includes one or more materials selected from a. group consisting of: a non-toxic food product, and a food additive; and
encapsulating DNA in said carrier to produce a universal microsphere stimulant.

29. The method of claim 28 wherein said carrier includes an FDA approved food additive.

30. The method of claim 28 wherein said carrier includes a kosher certified food additive.

31. The method of claim 28 further comprising encapsulating a protein in said carrier.

32. The method of claim 28 wherein said carrier includes food additives, and wherein said carrier encapsulates a protein and at least two unique DNA.

33. The method of claim 28 further comprising encapsulating antibody triggers in said carrier.

34. The method of claim 28 further comprising encapsulating fluorescent molecules in said carrier.

35. The method of claim 28 further comprising encapsulating antibody triggers in said carrier and encapsulating fluorescent molecules said carrier.

36. The method of claim 28 wherein said carrier has particle transport properties and further comprising encapsulating materials to alter said particle transport properties of said carrier in said carrier.

37. The method of claim 36 wherein said carrier has particle transport properties, and further comprising encapsulating materials to alter said particle transport properties of said carrier in said carrier wherein said materials to alter said particle transport properties are materials to alter charge.

38. The method of claim 28 wherein said carrier has particle transport properties and further comprising encapsulating materials to alter said particle transport properties of said carrier in said carrier wherein said materials to alter said particle transport properties are materials to alter density.

39. The method of claim 28 wherein said carrier has particle transport properties and further comprising encapsulating materials to control said particle transit properties of said carrier in said carrier.

40. The method of claim 28 further comprising encapsulating unique DNA having 100 bases in said carrier.

41. The method of claim 28 further comprising aerosoling said carrier and said encapsulated DNA producing an aersol form of said carrier and said encapsulated DNA and using said carrier and said encapsulated DNA in said aerosol form.

* * * * *